United States Patent
Clark et al.

(10) Patent No.: US 6,780,188 B2
(45) Date of Patent: Aug. 24, 2004

(54) ACL FIXATION PIN

(75) Inventors: Ron Clark, Pleasant Grove, UT (US); Jerry L. Lower, Bourbon, IN (US); Raymond E. Olsen, Smithfield, UT (US)

(73) Assignee: Ethicon, Inc., West Somerville, NJ (US)

( * ) Notice: Subject to any disclaimer, the term of this patent is extended or adjusted under 35 U.S.C. 154(b) by 191 days.

(21) Appl. No.: 10/028,504

(22) Filed: Oct. 22, 2001

(65) Prior Publication Data

US 2002/0058941 A1 May 16, 2002

Related U.S. Application Data

(62) Division of application No. 09/508,154, filed as application No. PCT/US98/19931 on Sep. 24, 1998, now Pat. No. 6,306,138.
(60) Provisional application No. 60/059,877, filed on Sep. 24, 1997, and provisional application No. 60/078,404, filed on Mar. 18, 1998.

(51) Int. Cl.$^7$ ............................................. A61B 17/86
(52) U.S. Cl. ........................................ 606/73; 606/232
(58) Field of Search ............................ 606/53, 60, 65, 606/72, 73, 86, 232

(56) References Cited

U.S. PATENT DOCUMENTS

| | | | |
|---|---|---|---|
| 2,382,019 A | 8/1945 | Miller | |
| 2,532,296 A | 12/1950 | Giesen | |
| 3,051,169 A | 8/1962 | Gustaf-Bertil | |
| 4,902,508 A | 2/1990 | Badylak et al. | |
| 4,927,421 A | 5/1990 | Goble et al. | |
| 4,950,270 A | 8/1990 | Bowman et al. | |
| 5,102,421 A | * 4/1992 | Anspach, Jr. | 606/232 |
| 5,139,520 A | 8/1992 | Rosenberg | |
| 5,211,647 A | 5/1993 | Schmieding | |
| RE34,293 E | 6/1993 | Goble et al. | |
| 5,266,075 A | 11/1993 | Clark et al. | |
| 5,281,422 A | 1/1994 | Badylak et al. | |
| 5,350,380 A | 9/1994 | Goble et al. | |
| 5,356,413 A | 10/1994 | Martins et al. | |
| 5,360,448 A | 11/1994 | Thramann | |
| 5,393,302 A | 2/1995 | Clark et al. | |
| RE34,871 E | 3/1995 | McGuire et al. | |
| 5,397,356 A | 3/1995 | Goble et al. | |
| 5,423,823 A | 6/1995 | Schmieding | |
| 5,431,651 A | 7/1995 | Goble | |
| 5,562,669 A | 10/1996 | McGuire | |
| 5,562,671 A | 10/1996 | Goble et al. | |
| 5,571,104 A | 11/1996 | Li | |

(List continued on next page.)

FOREIGN PATENT DOCUMENTS

FR 2 688 689 A 9/1993

*Primary Examiner*—Kevin Shaver
*Assistant Examiner*—Michael B. Priddy
(74) *Attorney, Agent, or Firm*—Barnes & Thornburg

(57) ABSTRACT

A pin (20) is provided for securing a replacement ligament (24) inside a tunnel (10) of a receptor bone (36). A threaded section (30) of the pin (20) engages and anchors the pin (20) in the receptor bone (36). A first taper (26) opposite the threaded section (30) is configured to enter a drilled hole (14) which is transverse to the tunnel (10), capture a looped replacement ligament (24), and extend into the medial side (25) of the receptor bone (36). A second taper (28) urges the replacement ligament (24) against the wall (15) of the tunnel (10) and provides resistance when the second taper (28) contacts the medial side (25) of the bone (36), thus signaling that the pin (20) has been inserted to the proper depth. The body (21) of the pin (20) secures the looped replacement ligament (24) in the tunnel (10) and holds the replacement ligament (24) in contact with the wall (15) of the tunnel (10) to insure ingrowth.

14 Claims, 5 Drawing Sheets

U.S. PATENT DOCUMENTS

| | | |
|---|---|---|
| 5,601,561 A | 2/1997 | Wolfe et al. |
| 5,601,562 A | 2/1997 | Wolf et al. |
| 5,643,268 A * | 7/1997 | Vilsmeier et al. ............. 606/73 |
| 5,711,969 A | 1/1998 | Patel et al. |
| 5,743,912 A | 4/1998 | Lahille et al. |
| 5,849,013 A | 12/1998 | Whittaker et al. |
| 5,871,504 A | 2/1999 | Eaton et al. |
| 5,931,840 A | 8/1999 | Goble et al. |
| 6,045,574 A | 4/2000 | Thal |
| 6,056,752 A | 5/2000 | Roger |
| 6,066,173 A | 5/2000 | McKernan et al. |
| 6,132,433 A | 10/2000 | Whelan |
| 6,162,225 A * | 12/2000 | Gertzman et al. ............ 606/73 |
| 6,221,107 B1 | 4/2001 | Steiner et al. |
| 6,585,740 B2 * | 7/2003 | Schlapfer et al. ............. 606/73 |

* cited by examiner

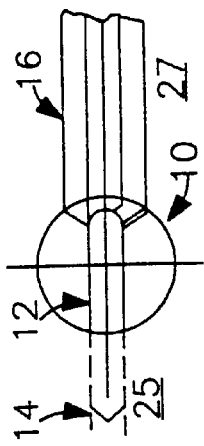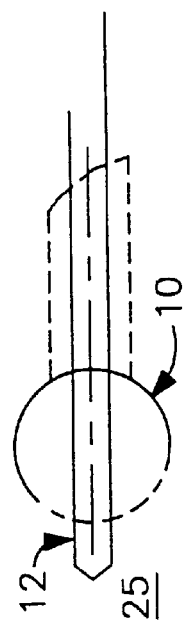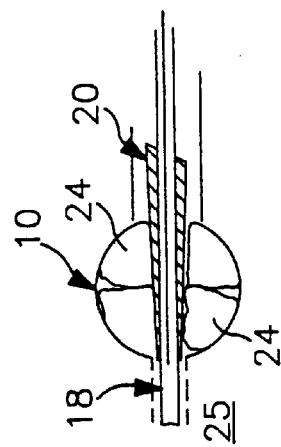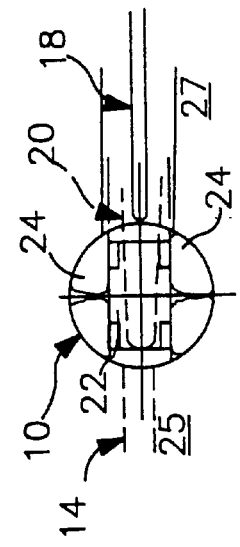

ACL FIXATION PIN

CROSS-REFERENCES TO RELATED APPLICATIONS

This application is a divisional of U.S. application Ser. No. 09/508,154, now U.S. Pat. No. 6,306,138, filed Mar. 7, 2000, which is a U.S. national application of international application serial No. PCT/US98/19931 filed Sep. 24, 1998, which claims priority to U.S. provisional applications serial Nos. 60/059,877 and 60/078,404 filed Sep. 24, 1997, and Mar. 18, 1998, respectively.

BACKGROUND AND SUMMARY OF THE INVENTION

The present invention relates to the anchoring of ligament replacements or soft tissue in bone tunnels, and more particularly to a cross pin and a method of fixing the cross pin which facilitates securing a replacement graft inside a bone and that promotes healing of the graft inside the bone.

When a ligament such as an anterior cruciate ligament (hereinafter "ACL") of a knee is damaged or torn, a replacement ligament is often installed in the knee to reconstruct the natural ACL. During such reconstruction, with the knee bent appropriately, a tunnel is typically drilled through the anterior portion of the tibia upwardly through the tibial plateau and into the distal end of the femur to approximate the natural position of the ACL, in accordance with well known surgical techniques. A bone-ligament-bone graft is then harvested, often from the patellar tendon following standard grafting techniques, all well known in the orthopaedic field. Typically, a wedge-shaped bone-ligament-bone graft is cut and contoured using a graft guide.

Various fixation methods are known in the orthopaedic field for securing a bone-ligament-bone graft within the tibia and femur so that the graft can heal. For example, it is known to use a pin installed transversely to the bone tunnel to secure the replacement ligament within the tunnel such as that shown in U.S. Pat. No. 5,397,356 entitled "Pin for Securing a Replacement Ligament to a Bone" to E. Marlowe Goble and Jerry L. Lower. Also, methods for installing such a cross pin are shown in U.S. Pat. No. 5,139,520 entitled "Method for ACL Reconstruction" to Thomas D. Rosenberg; U.S. Pat. No. 5,562,671 entitled "Ligament Replacement Cross Pinning Method" to E. Marlowe Goble and Jerry L. Lower; and U.S. Pat. No. 5,350,380 entitled "Method for Securing a Ligament Replacement in a Bone" to E. Marlowe Goble and Jerry L. Lower. The devices and methods disclosed in these patents are incorporated herein by reference. These types of pins often operate by holding and forcing the bone block at the end of the replacement ligament against the wall of the tunnel, essentially wedging the bone block in place. In other known methods, sutures coupled to the graft are anchored to the bone using screws or washers. The replacement ligaments can also be coupled directly to the bone using plates or washers in conjunction with a bone screw. Alternatively, the replacement ligament can be secured by interference screw fixation, as disclosed in U.S. Pat. No. 4,950,270 entitled "Cannulated Self-Tapping Bone Screw" to Jerald A. Bowman and Richard V. Zile.

Other materials which can be used as replacement ligaments include the gracilis tendon, semitendinosus tendon, and small intestine submucosa (hereinafter "SIS). U.S. Pat. No. 4,902,508 entitled "Tissue Graft Composition" to Stephen F. Badylak, et al.; U.S. Pat. No. 5,281,422 entitled "Graft for Promoting Autogenous Tissue Growth" to Stephen F. Badylak, et al.; and U.S. Pat. No. 5,611,969 entitled "Large Area Submucosal Tissue Graft Constructs" to Umesh H. Patel, et al. describe harvesting and preparation of SIS grafts. The methods and materials disclosed in these patents are incorporated herein by reference. While these graft materials perform well, prior art procedures for inserting and securing such material are time consuming. Also, in situations where previous reconstruction has been performed, a new femoral tunnel placed close to the previous tunnel may not allow for fixation methods such as interference screw fixation.

Replacement ligaments can be secured within the femoral tunnel without the use of a bone plug by looping the replacement ligament over a cross pin. A tendon threader, such as those described in U.S. Pat. No. 5,266,075 entitled "Tendon Threader for Endosteal Ligament Mounting" to Ron Clark and Raymond E. Olsen; and U.S. Pat. No. 5,601,562 entitled "Forked Insertion Tool and Method of Arthroscopic Surgery Using the Same" to Eugene M. Wolf and Richard D. Grafton, can be used to form a loop in the replacement ligament and to position the replacement ligament within the femoral tunnel so that the loop may be captured by the cross pin. The devices and methods disclosed in these patents are incorporated herein by reference.

Methods which use a cross pin to secure a looped replacement ligament are effective, especially in situations in which there had been a previous reconstruction. Unfortunately, existing cross pins were not designed for this purpose. Generally, they were designed to wedge a bone block into the medial wall of the bone tunnel. These pins were not designed to be inserted easily into a graft loop, and they were not designed to hold the graft material in contact with the femoral wall, which would insure better ingrowth.

The graft fixation method and cross pin of the present invention provide advantages over the prior fixation methods and pins. The pin includes two tapered portions, a body, and a threaded portion. In the illustrated embodiment, the first tapered portion is long, relatively narrow, has a gentle taper, and can be inserted easily through the transversely drilled hole and into the graft insertion tool, where it captures the loop of the replacement ligament more easily than prior pins. The first tapered portion also inserts easily into the medial side of the femur. Because the first tapered portion is relatively narrow, it may eliminate the need for a guidewire during insertion of the pin.

In the illustrated embodiment, the second tapered portion is substantially shorter and has a more severe taper than the first tapered portion. Also, as illustrated, the body portion is cylindrical, but body portions with other shapes may be acceptable. As the cross pin is inserted, the wider second tapered portion compresses the replacement ligament against the wall of the femoral tunnel. The body of the cross pin then holds the replacement ligament against the wall. Thus, the present invention insures better ingrowth and provides a more secure fixation technique than previously found. An additional advantage of the current invention is that the second tapered portion provides resistance when it meets the medial wall of the femoral tunnel, thus signaling when the cross pin is fully seated. Another advantage of the current fixation method and pin is that rigid fixation afforded by the cross pin allows the patient immediately to bear weight and start range of motion exercises.

Also in the illustrated embodiment, when the cross pin is fully seated, the threaded portion will be buried in the femur, and the proximal end of the cross pin will be flush with the lateral surface of the femur. However, a cross pin having a head which may protrude from the lateral surface of the femur is also within the scope of this invention. Such a head may aid in installation or may be useful for later removal of the pin.

The present invention also includes a method for installing the cross pin. By using the illustrated method, a surgeon may insert the looped replacement ligament into the femoral tunnel, capture the loop with the cross pin with relative ease, and seat the cross pin at the appropriate depth. The method results in a replacement ligament which is held securely in the femoral tunnel, in such a way as to insure rapid ingrowth.

Additional objects, features, and advantages of the present invention will become apparent from the following description of a preferred embodiment exemplifying the best mode of carrying out the invention as presently perceived.

BRIEF DESCRIPTION OF THE DRAWINGS

FIG. 1 is a cross-sectional view of a femoral tunnel showing a drill pin extending through the femoral tunnel into the medial side of the femoral tunnel;

FIG. 2 is a view similar to FIG. 1 showing the drill pin in a transverse tunnel across the femoral tunnel and into the medial side, and showing a cross pin reamer inserted over the drill pin and extending through the lateral side of the femoral tunnel;

FIG. 3 is a view similar to FIG. 2 after the drill pin and cross pin reamer are withdrawn from the transverse tunnel, a cross pin guidewire is inserted in the lateral side of the transverse tunnel, and a replacement ligament wrapped around a soft tissue tendon passer is inserted into the femoral tunnel;

FIG. 4 is a view similar to FIG. 3 after the tendon passer is removed from the femoral tunnel and showing the cross pin guidewire extending completely through a cross pin (in cross-section), through the femoral tunnel, through the replacement ligament looped over the cross pin, and into the medial side of the femoral tunnel;

DETAILED DESCRIPTION OF THE DRAWINGS

Figure 5:
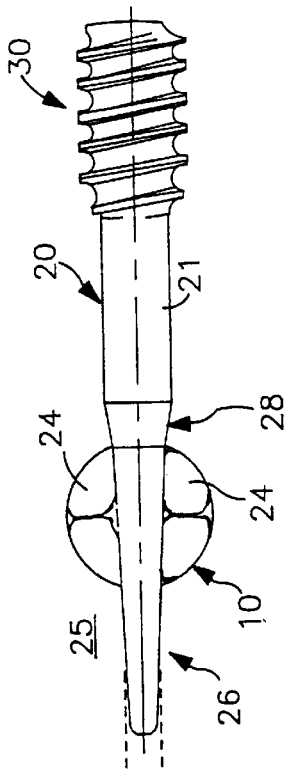
FIG. 5 is a view similar to FIG. 4 showing a first tapered portion of the cross pin just being inserted into a medial side of the femoral tunnel.
Figure 6:
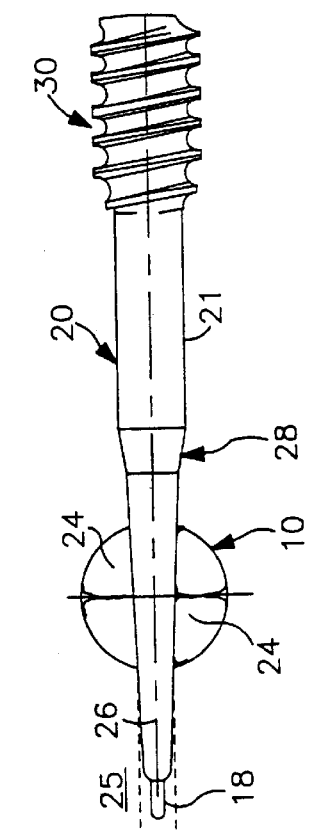
FIG. 6 shows the cross pin beginning to occupy an increasing portion of the femoral tunnel.
Figure 7:
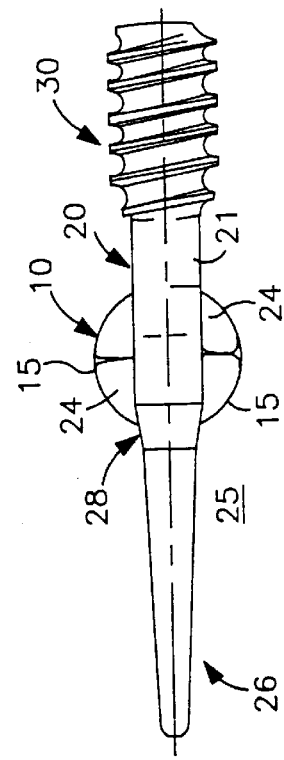
FIG. 7 shows further insertion of the cross pin through the femoral tunnel, such that a second tapered portion has entered the femoral tunnel and the second tapered portion has begun to hold the replacement ligament against the wall of the femoral tunnel.
Figure 8:
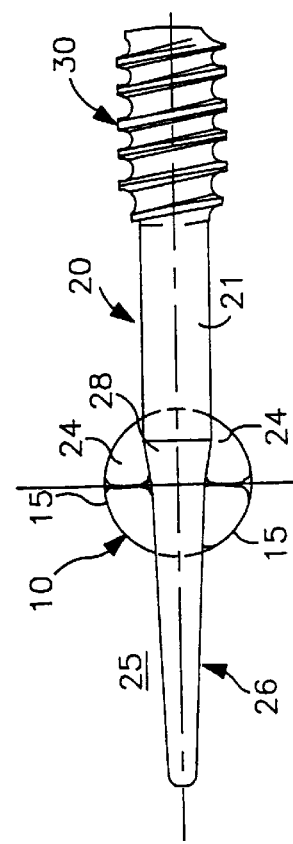
FIG. 8 shows the cross pin at a position of maximum insertion and tendon compression where the second tapered portion on cross pin is in contact with the medial side of the femoral tunnel, and the body on cross pin compresses the replacement ligament securely against the wall of the femoral tunnel.
Figure 9:
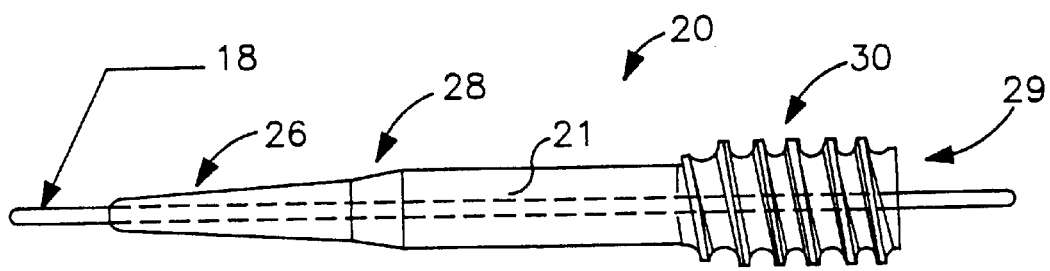
FIG. 9 is a side view of the cross pin and the cross pin guidewire in accordance with the present invention showing a proximal end of the cross pin having a threaded portion for securing the cross pin within the femur (not shown), two tapered portions, the first tapered portion being positioned at the distal end of the cross pin and proportioned and designed to slide within the tendon passer, through the looped replacement ligament, and into the medial side of the femoral tunnel, the second tapered portion of the cross pin being positioned adjacent to the first tapered portion and proportioned and designed to begin the process of holding the replacement ligament against the wall of the femoral tunnel and to provide resistance when it engages the medial side of the femoral tunnel, and a body proportioned and designed to hold the replacement ligament against the wall of the femoral tunnel for the purpose of ingrowth.
Figure 10:
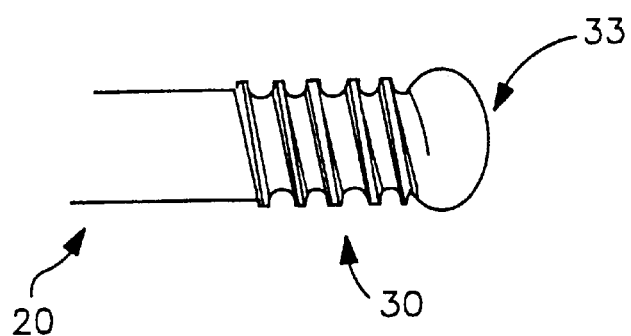
FIG. 10 is a side view of an alternative embodiment of the cross pin showing a head adjacent to the threaded portion.

In accordance with the present invention, a cross pin fixation system is provided for ACL reconstruction. In the method of the present invention, as illustrated, replacement ligaments of semitendinosus tendon, gracilis tendon, or SIS are used to replace the ACL. However, it is understood that other materials may be used as the replacement ligament within the scope of the invention. A looped replacement ligament 24 is inserted into the femoral tunnel 10. A cross pin 20 secures the replacement ligament 24 by holding the replacement ligament 24 against the wall 15 of a femoral tunnel 10. See FIG. 10. It will be appreciated that this holding action occurs in the illustrated embodiment by wedging and compressing the replacement ligaments against the wall of the femoral tunnel 10. The improved fixation method also secures the replacement ligament 24 by looping the replacement ligament 24 around the cross pin 20 itself. Thus, the replacement ligament 24 is secured over and around the cross pin 20 which is placed across the femoral tunnel 10 perpendicular to its axis. While the illustrated embodiment details a cross pin fixation method for ACL reconstruction, the pin and method of the present invention also may be used for other types of reconstruction. The graft fixation system of the present invention provides accurate and reproducible placement of the cross pin 20 while providing secure rigid fixation of the replacement ligament 24.

The fixation system of the present invention briefly includes the following steps and devices:

The present method for replacing the ACL begins with drilling a tunnel 11 through the tibia 34. Before drilling begins, a tibial guide pin (not shown) is inserted from the anteromedial tibia and exits on the tibial plateau. This tibial guide pin is then over-drilled with a reamer. A back cutting burr (not shown) then smooths the tunnel rim (not shown) of debris. The knee is flexed 90 to 110 degrees, and a femoral aimer (not shown) is used to locate a desired position of the femoral tunnel 10. Once the desired position has been secured, a threaded bayonet point pin with eyelet (not shown) is drilled into the femur 36 until it reaches the far cortex 13. Next, the femur 36 is drilled using a reamer 32. Ideally, a reamer should be used which is 9 or 10 mm wide, and the drilling should leave a femoral tunnel 10 which is 35 mm deep. Gradations along the reamer's shaft can be used to indicate the depth of the tunnel. Although some instruments described herein are not illustrated, all are commonly available and one of ordinary skill in the art will understand their use.

Figure 11:
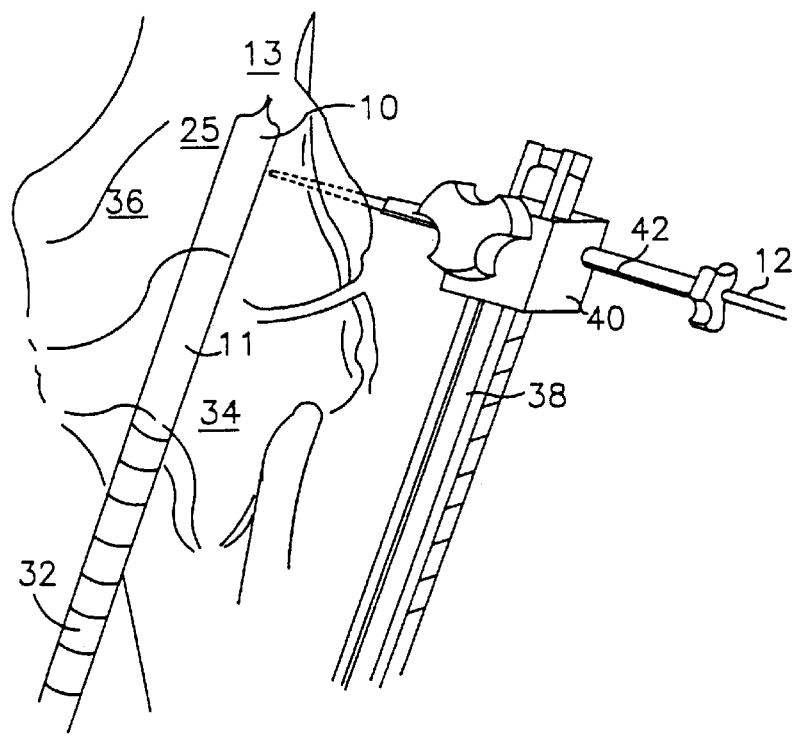
FIG. 11 is a view of a tibia and femur showing a reamer placed within the tibial tunnel and femoral tunnel, the reamer extending into the cortex of the femur, a ratcheting cannula positioned through a tunnel locator which is coupled to a cross pin guide, and a drill pin which is placed through the ratcheting cannula.
Figure 12:
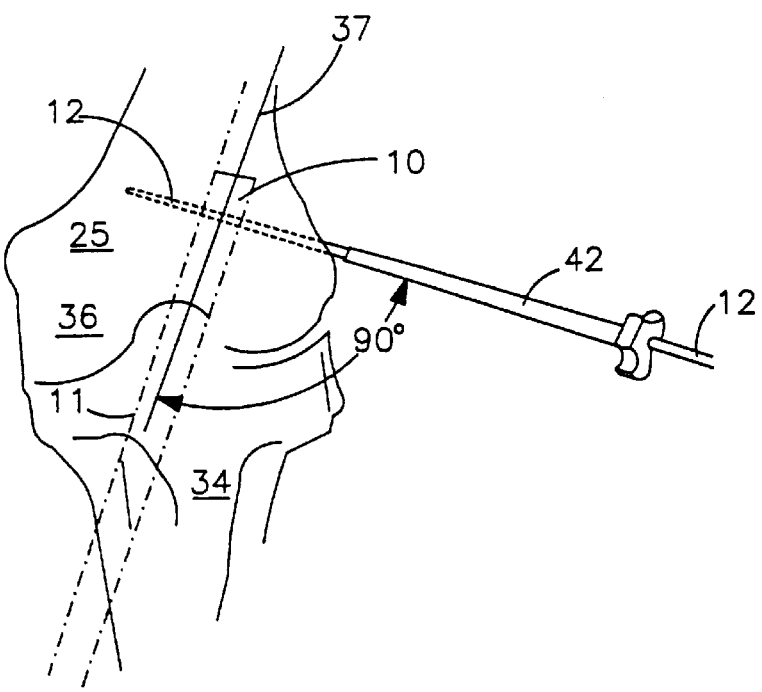
FIG. 12 is a view similar to FIG. 11 after the reamer has been removed from the femoral tunnel, showing the drill pin through the ratcheting cannula after the drill pin has drilled through the femoral tunnel and into the medial side of the femur, the drill pin intersecting the axis of the femoral tunnel.

Once the femoral tunnel 10 has been drilled, a cross pin guide 38 is attached directly to the reamer 32 and locked into place so that the cross pin guide 38 may rotate freely about the axis 37 of the femoral tunnel 10. As shown in FIG. 11, a tunnel locator 40 is mounted on the cross pin guide 38, and a ratcheting cannula 42 is inserted into the tunnel locator 40. Ideally, the cross pin guide 38 has graduations which indicate the distance in millimeters from the tip of the reamer in the femoral tunnel. Also ideally, the tunnel locator 40 is placed at the 15 mm mark.

The ratcheting cannula 42 is advanced until it contacts the skin. The cross pin guide 38 is then rotated away and an incision is made down to the bone. The cross pin guide 38 is rotated back into position and the ratcheting cannula 42 is advanced until it contacts the femoral cortex 13. A calibrated drill pin 12 is placed into the ratcheting cannula 42. Preferably, a 2.5 mm drill pin is used. The drill pin 12 also is advanced until it contacts the femoral cortex 13. The drill pin 12 is drilled into the femur 36 until it reaches the reamer 32, which is still located in the femoral tunnel 10. Calibrated markings on drill pin 12 allow the depth of penetration to be determined. The overall length of cross pin 20 and depth of the transverse tunnel 14 are determined by adding approximately 30 mm to the depth of penetration (reamer diameter plus 20 mm for the cross pin tip). The drill pin is then carefully withdrawn about 5 mm from the reamer.

The cross pin guide 38 (including the tunnel locator 40) and the reamer 32 (along with a reamer pin if it is still in the femoral tunnel) are removed from the femur 36, and the drill pin 12 is gently tapped until it appears in the femoral tunnel 10. The appearance of the drill pin 12 can be seen through the use of an arthroscope which is placed in the femoral tunnel 10. As it is advanced, the drill pin 12 should cross the center of the femoral tunnel 10, so that it intersects with the axis 37 of the femoral tunnel 10. If necessary, the reamer 32 is placed back into the femoral tunnel 10, the cross pin guide 38 is reattached to the reamer 32, and placement of the drill pin 12 is repeated. The drill pin 12 is then advanced into the medial side 25 of the femur 36, at least to the depth as calculated above. Next, a cannulated cross pin reamer 16 is used to enlarge the lateral side 27 of transverse tunnel 14 for insertion of the cross pin 20. Ideally, a soft tissue protector (not shown) is used in conjunction with the cross pin reamer 16.

Figure 13:
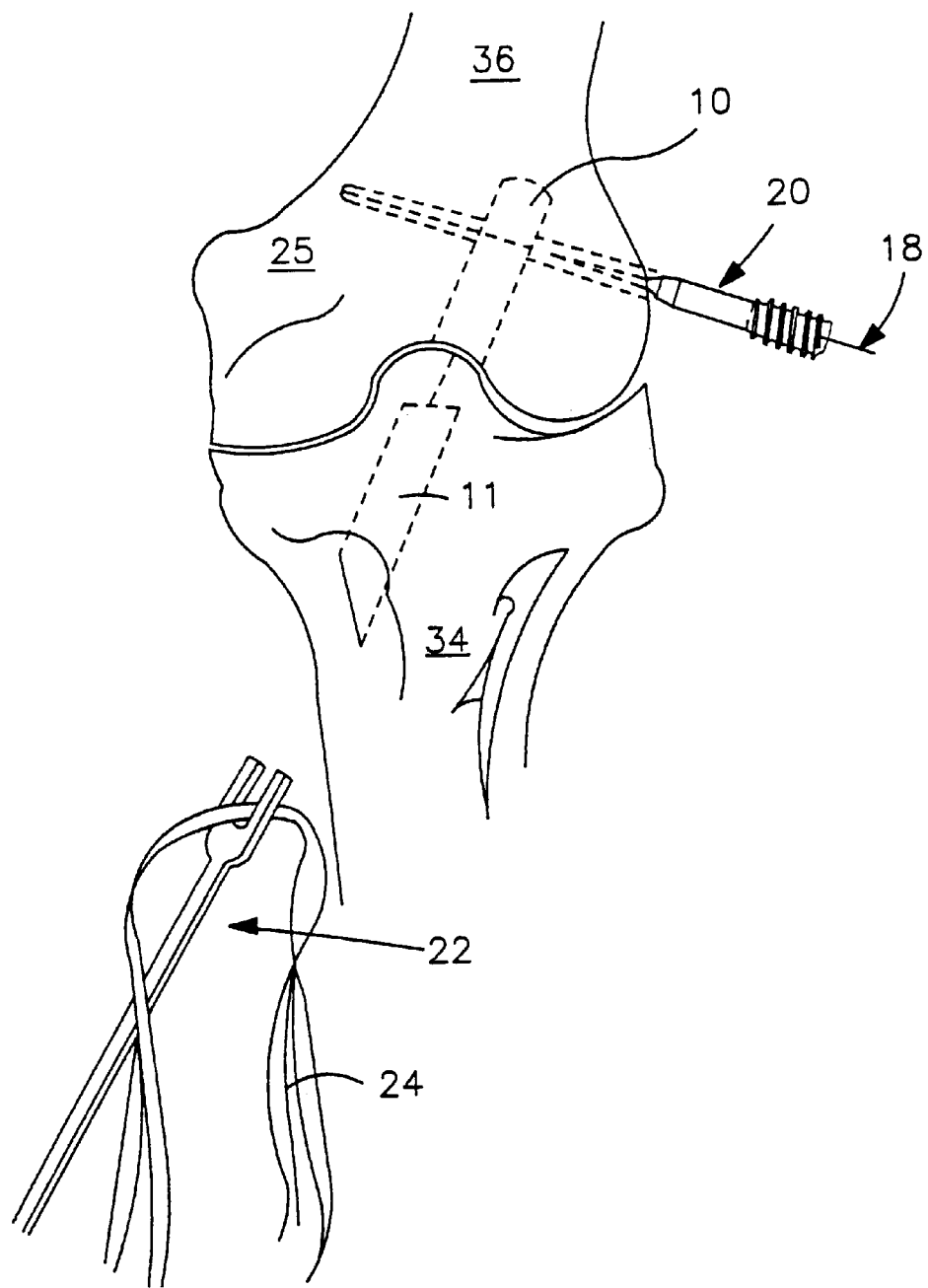
FIG. 13 is a view similar to FIG. 12 showing the cross pin over the guide wire as the cross pin is about to be inserted into the femur and also showing the tendon passer holding the replacement ligament to be inserted through the tibia and into the femoral tunnel.

Once the path has been enlarged, the drill pin 12 is withdrawn and a cross pin guidewire 18 is inserted through the cannulated cross pin reamer 16 and into the medial side 25 of the femur 36. With the guidewire 18 in place, the cross pin reamer 16 is removed and the cross pin 20 is advanced, distal end 31 first, over the guidewire 18, but not yet through the femoral tunnel 10. See FIG. 13. The guidewire 18 is then withdrawn from the femoral tunnel 10. Finally, the replacement ligament 24 is looped onto the tendon passer 22 and inserted through the tibial tunnel 11 and on into the femoral tunnel 10. A surgical lubricant may be used to ease passage. Ideally, a tendon passer 22 with a T-handle (not shown) is used, so that when the T-handle is parallel with the cross pin 20, the replacement ligament 24 is aligned such that further insertion of the cross pin 20 will capture the looped replacement ligament 24. The guidewire 18 is inserted back across the femoral tunnel 10 into the medial side 25 of the femur 36, and the tendon passer 22 is removed. At this point, it is necessary to make sure that the replacement ligament 24 has been captured over the guidewire 18. This can be done by gently pulling on the ends of the replacement ligament.

The cross pin 20 can now be advanced over the guidewire 18, preferably using a cannulated driver (not shown). As the cross pin 20 is advanced, the body 21 of the cross pin 20 acts to hold the replacement ligament 24 against the wall 15 of femoral tunnel 10 and, thus, insure better ingrowth. Once fully seated, the body 21 also acts to secure the looped replacement ligament 24 within the femoral tunnel. When the cross pin 20 can no longer be advanced, the cross pin 20 should be fully seated. This resistance represents the second tapered portion 28 engaging the medial wall 25 of the femoral tunnel 10. The guidewire 18 may then be removed. Because of the gradual taper of the first tapered portion 26, the guidewire 18 is not essential, and its use may be omitted. Finally, the replacement ligament 24 is secured on the tibial side by any of various known fixation methods.

In the illustrated embodiment, the threaded portion 30 of the proximal end 29 of the cross pin 20 will bury into the femur 36 because the length has been custom determined for each patient. However, the cross pin 20 in accordance with the present invention is placed into the femur 36 in such a position that the cross pin 20 may be retrieved from the femur 36 after the replacement ligament 24 has healed into the bone. It is understood that a cross pin 20 with a head 33 adjacent to the threaded portion 30 will operate in the same manner. See FIG. 10. Also, the cross pin 20 used in the fixation system of the present invention provides high graft pull out values. Finally, the cross pin 20 effectively attaches the replacement graft close to the anatomic origin of the ACL on the femur 36.

Although the invention has been described with reference to several embodiments, variations and modifications exist within the scope and spirit of the invention as described.

What is claimed is:

1. A pin for securing a replacement ligament inside a tunnel of a receptor bone, the pin comprising:
    a body having a distal end and a proximal end,
    a threaded portion positioned at the proximal end,
    a first tapered portion positioned at the distal end, and
    a second tapered portion positioned adjacent to the first tapered portion, between the first tapered portion and the threaded portion but spaced from the threaded portion.

2. The pin of claim 1, wherein the first tapered portion and the second tapered portion each have a distal end and a proximal end and increase radially from the distal end to the proximal end.

3. The pin of claim 2, wherein the first tapered portion is axially relatively long, and a diameter of the first tapered portion increases gradually from the distal end to the proximal end.

4. The pin of claim 3, wherein the second tapered portion is axially relatively short, and the diameter of the second tapered portion increases rapidly from the distal end to the proximal end.

5. The pin of claim 4, wherein the body is substantially cylindrical and has a diameter substantially equal to that of the proximal end of the second tapered portion.

6. A pin for securing and positioning a replacement ligament in a bone tunnel of a receptor bone, the pin comprising:
    a distal end, a body portion, and a proximal end,
    a first tapered portion positioned at the distal end, the first tapered portion extending toward the body portion and increasing in diameter closer to the body portion, a second tapered portion positioned between the first tapered portion and the body portion, the second tapered portion increasing in diameter closer to the body portion, wherein the second tapered portion has a taper that is different from a taper of the first tapered portion, and a threaded portion at the proximal end, adjacent to the body portion, the threaded portion for securing the pin within the receptor bone.

7. The pin of claim 6, wherein the taper of the first tapered portion is an axially long, radially narrow taper, and the taper of the second tapered portion is an axially short, radially wide taper.

8. The pin of claim 7, wherein the body portion is substantially cylindrical.

9. The pin of claim 7, further comprising a head, the head positioned at the proximal end, and the threaded portion positioned between the head and the body.

10. The pin of claim 6, further comprising a head, the head positioned at the proximal end, and the threaded portion positioned between the head and the body portion.

11. A pin for securing and positioning a replacement ligament in a femoral bone tunnel of a receptor bone, the pin comprising:

a distal end and a proximal end, a body portion extending between the distal end and the proximal end, the body portion proportioned and designed to secure the replacement ligament within the femoral bone tunnel and to hold the replacement ligament in contact with the receptor bone, a first tapered portion positioned at the distal end, the first tapered portion extending toward the body portion and increasing in diameter closer to the body portion, the first tapered portion proportioned and designed to extend beyond the femoral bone tunnel and into the medial side of the femoral tunnel, a second tapered portion positioned between the first tapered portion and the body portion, the second tapered portion increasing in diameter closer to the body portion, the second tapered portion proportioned and designed to urge the replacement ligament toward the receptor bone as the pin is inserted into the receptor bone and engage the medial side of the femoral tunnel when the pin is inserted completely, wherein the second tapered portion has a taper that is different from a taper of the first tapered portion, and a threaded portion positioned at the proximal end, adjacent to the body portion, the threaded portion proportioned and designed to secure the pin within the receptor bone.

12. The pin of claim 11, wherein the first tapered portion is axially long and the taper of the first portion is radially narrow, and the second tapered portion is axially short and the taper of the second portion is greater radially than the taper of the first tapered portion.

13. The pin of claim 11, further comprising a head, the head being positioned at the proximal end, and the threaded portion being positioned between the head and the body portion.

14. A pin for securing a looped replacement ligament inside a tunnel of a receptor bone of a patient, the pin comprising:

a body having a distal end and a proximal end, the body including means for engaging the receptor bone to anchor the pin in the receptor bone, such means being positioned at the proximal end, means for securing the looped replacement ligament in the receptor bones and for holding the looped replacement ligament in contact with the receptor bone, means for providing resistance when the pin is inserted fully within the receptor bone, said means including a tapered portion that is axially relatively short, and means for inserting the pin through the looped replacement ligament and into the medial side of the receptor bone, such means being positioned at the distal end.

* * * * *